(12) United States Patent
Bombardelli et al.

(10) Patent No.: US 7,683,163 B2
(45) Date of Patent: Mar. 23, 2010

(54) COLCHICOSIDE ANALOGUES

(75) Inventors: Ezio Bombardelli, Groppello Cairoli (IT); Gabriele Fontana, Milan (IT)

(73) Assignee: Indena S.p.A., Milan (IT)

( * ) Notice: Subject to any disclaimer, the term of this patent is extended or adjusted under 35 U.S.C. 154(b) by 593 days.

(21) Appl. No.: 10/559,462

(22) PCT Filed: May 26, 2004

(86) PCT No.: PCT/EP2004/005645

§ 371 (c)(1),
(2), (4) Date: May 19, 2006

(87) PCT Pub. No.: WO2004/111068

PCT Pub. Date: Dec. 23, 2004

(65) Prior Publication Data

US 2007/0129315 A1    Jun. 7, 2007

(30) Foreign Application Priority Data

Jun. 6, 2003    (IT) ................. MI2003A1144

(51) Int. Cl.
C07H 17/02 (2006.01)
A01N 43/04 (2006.01)
A61K 31/70 (2006.01)

(52) U.S. Cl. ................. 536/17.9; 514/33

(58) Field of Classification Search ........... None
See application file for complete search history.

(56) References Cited

U.S. PATENT DOCUMENTS 5,777,136 A * 7/1998 Bombardelli ............ 549/417
5,843,910 A * 12/1998 Bombardelli et al. ........ 514/33
6,150,140 A * 11/2000 Bombardelli et al. ........ 435/74

FOREIGN PATENT DOCUMENTS

| CH | 341 831 A | 10/1959 |
| EP | 0 789 028 A | 8/1997 |
| GB | 773729 A * | 5/1957 |

* cited by examiner

Primary Examiner—Shaojia Anna Jiang
Assistant Examiner—Layla Bland
(74) Attorney, Agent, or Firm—Young & Thompson

(57) ABSTRACT

The present invention relates to colchicine derivatives, in particular to the 3-demethyl and 3-demethylthio-colchicine of the general formula (I) in which X is oxygen or sulfur, a method for the preparation thereof and pharmaceutical compositions containing them. The compounds of formula (I) have muscle relaxing, anti-inflammatory and anti-gout activity.

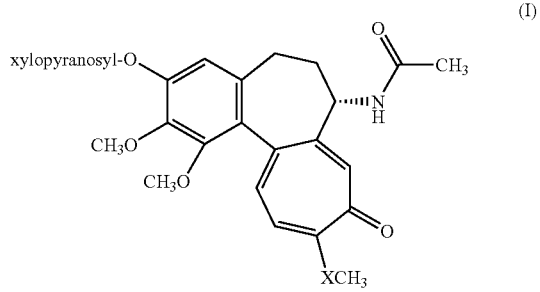

(I)

15 Claims, No Drawings

COLCHICOSIDE ANALOGUES

FIELD OF THE INVENTION

The present invention relates to colchicine derivatives, in particular 3-demethyl- and 3-demethylthio-colchicine derivatives with muscle relaxant, anti-inflammatory and anti-gout activity.

TECHNOLOGICAL BACKGROUND

Relaxant drugs reduce muscle tone and are used in therapy for the treatment of contractures and muscle spasm. Muscle spasm is one of the main factors responsible for chronic pain; it characterises several pathologies of the locomotor apparatus as well as inflammatory-rheumatic and degenerative orthopaedic pathologies; when it affects articulations, further to pain, it causes rigidity, which reduces joint mobility and flexibility in the affected part. For these reasons, the study of molecules endowed with muscle relaxant and antispasmodic properties still raises remarkable clinical interest.

As it is known, colchicine is a pseudoalcaloid that has been widespreadly used for some time for the treatment of gout. The use of 3-demethyl-thiocolchicine glucoside, thiocolchicoside, is also widespread in therapy for treating contractures and inflammatory conditions that affect the muscular system (Ortopedia e traumatologia Oggi XII, n. 4, 1992). It has been recently shown that the activity of thiocolchicoside is due to its ability to interact with strychnine-sensitive glycine receptors; therefore, compounds having glycine-mimicking activity can be used in the rheumatologic-orthopaedic field, due to their muscle relaxant properties.

DISCLOSURE OF THE INVENTION

The present invention relates to colchicine derivatives of the general formula (I):

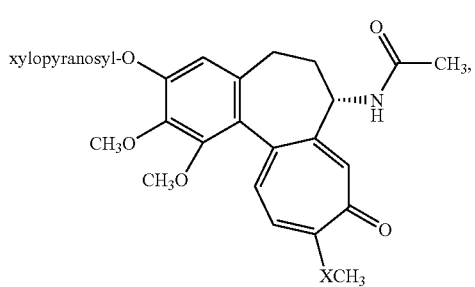

(I)

in which X is oxygen or sulfur.

For the purposes of the present description, the compound in which X is oxygen is referred to as (Ia), whereas the compound of formula (I) in which X is sulfur is referred to as (Ib). D and L isomers are comprised in the compounds of formula (I). The D and L isomers of compound (Ib), 3-O-β-D-xylopyranosyl-3-O-demethylthiocolchicine and 3-O-β-L-xylopyranosyl-3-O-demethylthiocolchicine are particularly preferred.

The compounds of the present invention are prepared by reaction of D- or L-xylopyranosyl-fluoride with 3-O-demethylcolchicine (IIa) and 3-O-demethylthiocolchicine (IIb)

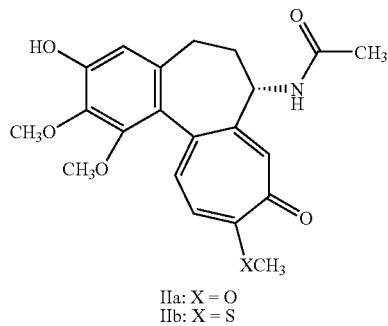

IIa: X = O
IIb: X = S according to the general method disclosed in EP 0 789 028.

In more detail, 3-O-demethylcolchicine (IIa) or 3-O-demethylthiocolchicine (IIb) are reacted with D- or L-xylopyranosyl-fluoride (III) or a protected form thereof, preferably peracetate. The reaction is carried out in polar aprotic solvents, preferably selected from acetonitrile and chlorinated solvents, at temperatures ranging from 0° C. to the boiling temperature of the solvent, preferably at room temperature, and in the presence of a base, preferably 1,1,3,3-tetramethylguanidine. The reaction is usually complete in a time ranging from 10 minutes to 2 hours. Hydrolysis of the protective groups can be carried out without recovery of the intermediates.

In particular, it has been observed that the β-D isomer of compound (Ib) has a significant muscle relaxant activity, higher than that of the corresponding thiocolchicoside isomer, and is also endowed with a significant anti-inflammatory and anti-gout activity.

Muscle relaxant activity was evaluated with the rota-rod test. Swiss male mice weighing 20-25 g were treated intraperitoneally with the β-D isomer of compound (Ib) at doses of 1-3-10 mg/kg, thirty minutes before the test. Relaxant activity on striated muscles was evaluated by testing the resistance of the mice to the stimuli of a rotating plane revolving at increasing rate, from 2 to 50 r.p.m. The results reported in the following table show that the compound of the present invention is more active than thiocolchicoside used as the reference compound.

TABLE 1

| Treatment | Dose (mg/Kg i.p.) | Resistance time (sec. M ± S.E.) | $DE_{50}$ mg/Kg |
| --- | --- | --- | --- |
| Controls | | 400 ± 27 | |
| Compound (Ib) isomer β-D | 1 | 270 ± 19 | |
| | 3 | 175 ± 14 | 2.23 (1.84-2.82) |
| | 10 | 80 ± 10 | |
| Thiocolchicoside isomer β-D | 1 | 345 ± 20 | |
| | 3 | 265 ± 17 | 4.47 (3.16-7.01) |
| | 10 | 110 ± 12 | |

Moreover, the compound of the invention is significantly less toxic. In fact, its $DL_{50}$ is 80 (63-94) mg/kg i.p., whereas the $DL_{50}$ of thiocolchicoside is 20 mg/kg. These results show that the compound of the invention, further to being more active, has a toxic/active dose ratio significantly more favourable than thiocolchicoside.

TABLE 2

| Treatment | DE$_{50}$ mg/kg i.p. | DL$_{50}$ mg/kg i.p. | DL$_{50}$/DE50 |
|---|---|---|---|
| Compound (Ib) isomer β-D | 2.23 | 80 | 35.87 |
| Thiocolchicoside isomer β-D | 4.47 | 20 | 4.47 |

The compounds of the invention can be incorporated in pharmaceutical formulations intended to oral, intravenous, intramuscular, transdermal and topical administration with conventional excipients and methods, such as those reported in Remington's Pharmaceutical Sciences Handbook, XVII Ed., Mack Pub., N.Y., U.S.A. Among the excipients useful for the preparation of liposomial forms for the parenteral or topical administration, natural and synthetic phospholipids are particularly preferred. The doses can range from 5 to 50 mg a day depending on the disease and the administration route.

The invention will be now illustrated in greater detail by means of some examples.

EXPERIMENTAL SECTION

Melting points were measured with a Buchi 510 apparatus. NMR spectra were recorded with a Bruker AC 200.

Example 1

3-O-(2',3',4'-O-triacetyl-β-D-xylopyranosyl)-3-O-demethylthiocolchicine

3-O-Demethylthiocolchicine (IIb) (0.5 mmoles) and 2,3,4-O-triacetyl-α-D-xylopyranosyl fluoride (0.75 mmoles), prepared according to Hayashi et al. (*Chemistry Lett.* 1984, 1747), were suspended in dry acetonitrile at room temperature (10 ml), under nitrogen and with stirring. 1,1,3,3-Tetramethylguanidine (1.5 mmoles) was added and the suspension turned clear red. Boron trifluoride etherate (4 mmoles) was added, thereafter the solution turned colourless. The reaction was monitored by TLC (CH$_2$Cl$_2$:MeOH 9:1). After disappearance of the starting products (30 min), the reaction was quenched adding a saturated sodium bicarbonate solution (10 ml). The phases were separated and the aqueous one was extracted with ethyl acetate (3×10 ml). The combined organic phases were washed with a saturated potassium hydrogen sulfate solution (15 ml), brine (15 ml) and dried over magnesium sulfate. After evaporation of the solvent, the reaction products were separated by chromatography on silica gel. Alternatively, the crude was directly subjected to deprotection.

$^1$H-NMR (CDCl$_3$)-δ (ppm) 7.06 (NH, d, 7.4 Hz), 7.06 (H12, d, 10.3 Hz), 7.27 (H11. d, 10.3 Hz), 7.33 (H8, s), 6.71 (H4, s), 4.71-4.55 (H7, m), 2.60-1.90 (H5-H6, m), 3.90 (2-OMe, s), 3.66 (1-OMe, s), 2.44 (SMe, s), 2.00 (acetamide), 5.28-5.18, 5.08-4.98 (H1', H2', H3', H4', m), 4.30 (H5'a, ddd, 4.3, 7.0, 12.1 Hz), 3.58 (H5'b, ddd 4.3, 7.0, 12.1 Hz), 2.12 (OAc), 2.11 (OAc), 2.10 (OAc).

Example 2

3-O-(2',3',4'-O-triacetyl-β-L-xylopyranosyl)-3-O-demethylthiocolchicine

3-O-Demethylthiocolchicine (IIb) (0.5 mmoles) and 2,3,4-O-triacetyl-α-L-xylopyranosyl fluoride (0.75 mmoles), prepared according to Takanashi et al. (*Liebigs Ann. Chem.* 1997, 1081), were suspended in dry acetonitrile at room temperature (10 ml), under nitrogen and with stirring. 1,1,3,3-Tetramethylguanidine (1.5 mmoles) was then added and the suspension turned clear red. After addition of boron trifluoride etherate (4 mmoles) the solution turned colourless. The reaction was monitored by TLC (CH$_2$Cl$_2$:MeOH 9:1). After disappearance of the starting material (2 hours), the reaction was quenched by addition of a saturated sodium bicarbonate solution (10 ml). The phases were separated and the aqueous one was extracted with ethyl acetate (3×10 ml). The combined organic phases were washed with a potassium hydrogen sulfate saturated solution (15 ml), brine (15 ml) and dried over magnesium sulfate. After evaporation of the solvent, the reaction products were separated by chromatography on silica gel. Alternatively, the crude was directly subjected to deprotection.

$^1$H-NMR (CDCl$_3$)-δ (ppm) 7.34 (NH, d, 7.9 Hz), 7.07 (H12, d, 10.7 Hz), 7.30 (H11, d, 10.7 Hz), 7.37 (H8, s), 6.71 (H4, s), 4.71-4.55 (H7, m), 2.60-1.80 (H5-H6, m), 3.88 (2-OMe, s), 3.64 (1-OMe, s), 2.44 (SMe, s), 2.00 (acetamide), 5.28-5.18 e 5.10-4.90 (H1', H2', H3', H4' m), 4.25 (H5'a, ddd, 4.3, 4.4, 12.1 Hz), 3.58 (H5'b, ddd 4.3, 4.4, 12.1 Hz), 2.14 (OAc), 2.11 (OAc), 2.10 (OAc).

Example 3

General Method for Deprotection in Ethanol

The crude product (0.5 theoretical mmoles) from example 1 or 2 was dissolved in ethanol (4 ml) and 1N NaOH (2 ml) at room temperature. The reaction was checked by TLC. After disappearance of the starting product the solvent was evaporated off and the residue was subjected to silica gel chromatography. The product can be further crystallized from methanol/isopropanol.

Example 4

General Method for Deprotection in Acetone

The crude product from example 1 or 2 (1 theoretical mmol) was suspended with potassium carbonate in acetone (30 ml) and water (10 ml). The mixture was refluxed until disappearance of the starting product. The solvent was evaporated off and the product recovered by chromatography. The product can be further crystallized from methanol and diisopropyl ether.

Example 5

3-O-β-D-xylopyranosyl-3-O-demethylthiocolchicine

The product was obtained according to the deprotection method of example 3 or 4 with 45% yield, after chromatography on silica gel eluting with a CH$_2$Cl$_2$/MeOH gradient.

m.p. 193° C.; [α]$_D^{22}$-201 (c 1, MeOH);

$^1$H-NMR (CDCl$_3$): ppm 8.64 (NH, d, 7.6 Hz), 7.15 (H12, d, 10.6 Hz), 7.28 (H11, d, 10.6 Hz), 7.03 (H8, s), 6.85 (H4, s)

4.37-4.25 (H7, m), 2.60-1.80 (H5-H6, m), 3.84 (2-OMe, s), 3.55 (1-OMe, s), 2.42 (SMe, s), 1.86 (acetamide), 4.97 (H1', 6.6 Hz), 3.20-3.90 (H2', H3', H4', H5', m), 4.40-5.60 (OH).

Example 6

3-O-β-L-xylopyranosyl-3-O-demethylthiocolchicine

The product was obtained according to the deprotection method of example 3 or 4 with 45% yield, after chromatography on silica gel eluting with a CH$_2$Cl$_2$/MeOH gradient.
m.p. 220° C.; $[\alpha]_D^{22}$-176 (c 1, MeOH);
$^1$H-NMR (CDCl$_3$): ppm 8.64 (NH, d, 7.3 Hz), 7.17 (H12, d, 10.2 Hz), 7.29 (H11, d, 10.2 Hz), 7.03 (H8, s), 6.87 (H4, s) 4.23-4.41 (H7, m), 2.70-1.90 (H5-H6, m), 3.84 (2-OMe, s), 3.55 (1-OMe, s), 2.42 (SMe, s), 1.86 (acetamide), 5.02 (H1', 6.9 Hz), 3.20-3.90 (H2', H3', H4', H5', m), 4.90-5.60 (OH).

The invention claimed is:

1. A compound of the general formula (I):

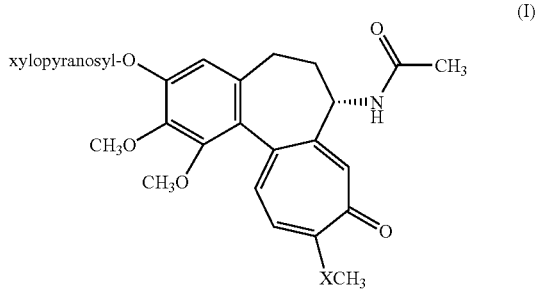

in which X is oxygen or sulfur.

2. The compound as claimed in claim 1 wherein X is oxygen.

3. The compound as claimed in claim 1 wherein X is sulfur.

4. A compound selected from the group consisting of 3-O-β-D-xylopyranosyl-3-O-demethylthiocolchicine and 3-O-β-L-xylopyranosyl-3-O-demethylthiocolchicine.

5. A medicament comprising a compound of the general formula (I):

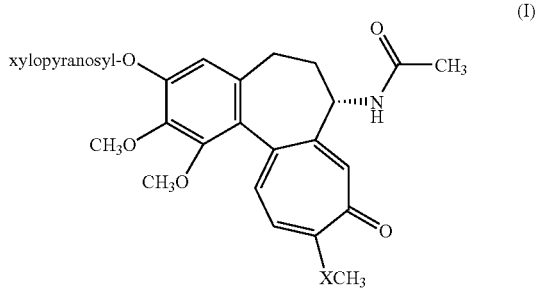

in which X is oxygen or sulfur.

6. A pharmaceutical composition containing a compound of the general formula (I):

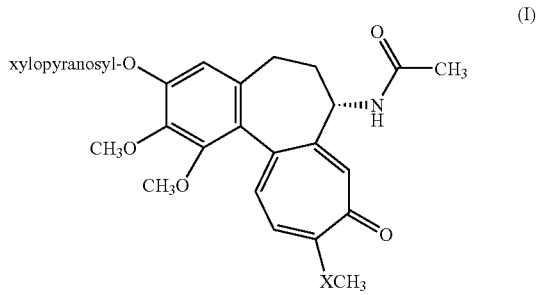

in which X is oxygen or sulfur, the compound being in admixture with suitable excipients and/or carriers.

7. The pharmaceutical composition as claimed in claim 6, in topical form.

8. The pharmaceutical composition as claimed in claim 6 in parenteral form.

9. The pharmaceutical composition as claimed in claim 7 in which the excipients are selected from natural and synthetic phospholipids.

10. A method for preparing of a muscle relaxant medicament, comprising adding the compound according to claim 1 to an excipient.

11. A method for preparing an anti-inflammatory medicament, comprising adding the compound according to claim 1 to an excipient.

12. A method for preparing anti-gout medicaments, comprising adding the compound according to claim 1 to an excipient.

13. A method treating gout, comprising administering to a subject in need thereof an effective amount of a compound according to claim 1.

14. A method for treating an inflammation, comprising administering to a subject in need thereof an effective amount of a compound according to claim 1.

15. A method for relaxing muscles, comprising administering to a subject in need thereof an effective amount of a compound according to claim 1.

* * * * *